United States Patent [19]

Buttram et al.

[11] Patent Number: 5,092,176
[45] Date of Patent: Mar. 3, 1992

[54] METHOD FOR DETERMINING DEPOSIT BUILDUP

[75] Inventors: Jonathan D. Buttram, Villamont; William E. Lawrie, Concord; Daniel M. Schlader, Forest, all of Va.

[73] Assignee: The Babcock & Wilcox Company, New Orleans, La.

[21] Appl. No.: 546,283

[22] Filed: Jun. 29, 1990

[51] Int. Cl.⁵ .................................... G01N 9/24
[52] U.S. Cl. ........................................ 73/599
[58] Field of Search ............... 73/599, 600, 622, 637, 73/645, 646, 597

[56] References Cited

U.S. PATENT DOCUMENTS

| 4,669,310 | 6/1987 | Lester | 73/597 |
| 4,685,334 | 8/1987 | Latimer | 73/599 |

OTHER PUBLICATIONS

Gordon, Jr., B. E., *Measurement of Applied and Residual Stresses Using an Ultrasonic Instrumentation System*, ISA Transactions, vol. 19, No. 2, pp. 33-40, presented at the ISA Symposium 1978, Albuquerque.

*Mitigating Forced Outages By Selective Replacement of Boiler Tubes*, Loper, Schoemaker, and Stromp, Technical Article presented at EPRI in Bel Harbor, Fla., Apr. 13-15, 1983.

*Ultrasonic Detection of Calcium Sulfate Scale on Metal Surfaces*, by Fred R. Rollins, Jr., U.S. Department of Interior, Office of Saline Water, Research and Development Progress Report No. 444.

Primary Examiner—Hezron E. Williams
Assistant Examiner—Louis M. Arana
Attorney, Agent, or Firm—Vytas R. Matas; Robert J. Edwards; Daniel S. Kalka

[57] ABSTRACT

A method of determining low density deposits on the inner surface of a boiler tube comprises the generation of ultrasonic energy which is directed from the outer surface of the tube to the inner surface of the tube. The energy is reflected back and forth between the inner and outer surfaces with each reflection of the inner surface loosing energy by attenuation into any existing low density deposit. The first and fourth reflections are measured and digitized for analysis to determine the amount of attenuation. The amount of attenuation is representative of the low density deposit on the inner surface of the tube. The tube is preferably empty of water to avoid transmission of ultrasonic energy through water in the tube.

6 Claims, 1 Drawing Sheet

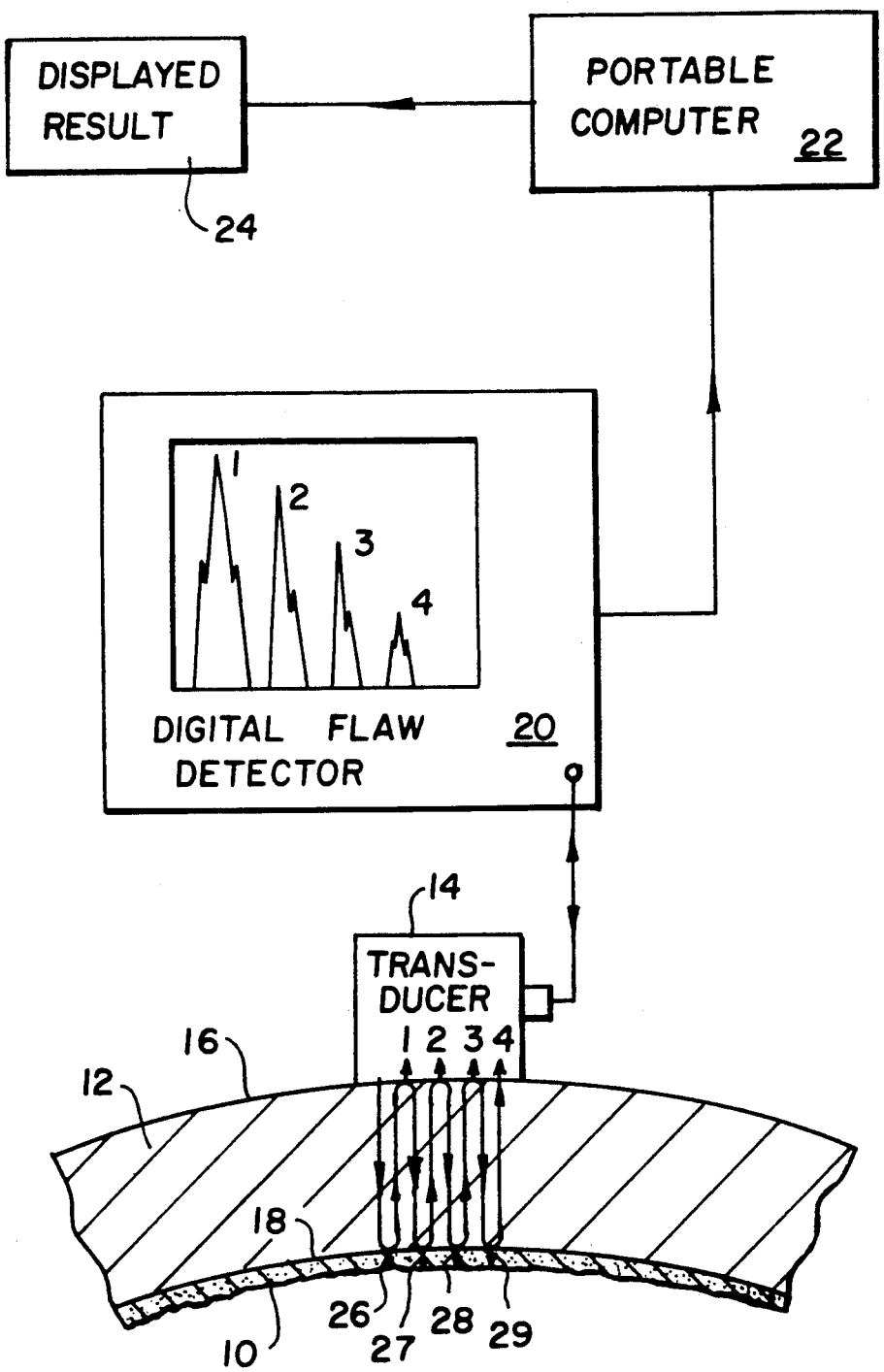

METHOD FOR DETERMINING DEPOSIT BUILDUP

FIELD AND BACKGROUND OF THE INVENTION

The present invention is directed to an ultrasonic method for quantifying the amount of low density deposit on the inner surface of boiler waterwall tubes.

Deposits in waterwall tubing can be characterized according to density and chemical composition. Such deposits are generally of the same chemical makeup which is magnetite ($Fe_3O_4$), however, their densities vary considerably due to differences in porosity levels. Presently, a service referred to as NOTIS TM is applied to "high" density deposits in steam-filled tubes (e.g. reheater or superheater tubes). Steamside oxide deposits have a density of greater than 90% of the theoretical density of magnetite which is 5.18 gm/cc. The amount of porosity contained in steamside scale is low, therefore an ultrasonic pulse can travel through this medium with little resistance. U.S. Pat. No. 4,669,310 disclosed the NOTIS TM service which uses ultrasonic analysis.

In the case of "low" density deposits or waterside oxide, which grows in furnace waterwalls, the porosity level is high. Waterside deposit density is 50% (±20%) of magnetite's theoretical density. With this amount of porosity, an ultrasonic pulse has difficulty finding a continuous medium for travel. As the pulse collides with the individual pores, pulse energy is dissipated, decreasing its capability to travel further into the deposit. The greater the porosity, the shorter the travel.

The NOTIS TM service and U.S. Pat. No. 4,669,310 measures "high" density deposits and involve determining the pulse travel time between individual signals thus generating a quantitative result, e.g. in mils of oxide.

U.S. Pat. No. 4,685,334 relates to the ultrasonic detection of hydrogen damage in boiler tubes. This reference teaches the use of angle-beam ultrasonic shear-waves introduced via a pitch-catch technique in either the axial or the circumferential directions of a boiler tube to detect the presence of hydrogen damage. The differences in relative attenuation in scanning occurring in an undamaged area and a hydrogen damaged area are used to detect hydrogen damage.

U.S. Pat. No. 3,901,071 is directed to an ultrasonic thickness gauge having ultrasonic probes positioned around the circumferences of a pipe to monitor the pipe thickness by the time interval between echoes from the outer and inner surfaces of the pipe.

U.S. Pat. No. 4,446,736 describes an ultrasonic method for testing the integrity of the internal lining of a hollow body. This reference teaches that a lining that is intact will absorb the ultrasonic wave and will not reflect the wave. Accordingly, a reflected wave frequently indicates a loss of the lining on the adjacent wall. Comparison of the reflected wave with predetermined standards provides an indication on whether or not the lining is intact.

In addition, the following technical references are pertinent to the present invention:

1. Gordon, Jr., B. E., *Measurement of Applied and Residual Stresses Using an Ultrasonic Instrumentation System*, ISA Transactions, Vol. 19, No. 2, pages 33-40, presented at the ISA Symposium 1978, Albuquerque.
2. *Mitigating Forced Outages By Selective Replacement of Boiler Tubes*, Loper, Schoemaker, and Stromp, Technical Article presented at EPRI in Bel Harbor, Fla., Apr. 13-15, 1983.
3. *Ultrasonic Detection of Calcium Sulfate Scale on Metal Surfaces*, by Fred R. Rollins, Jr., U.S. Department of Interior, Office of Saline Water, Research and Development Progress Report No. 444.

Technical reference 1 relates to an ultrasonic inspection system developed for nondestructive measurement of applied and residual stresses. The system measures time of flight of an ultrasonic pulse through a material.

Technical reference 2 discloses a method of inspecting boiler tubes for hydrogen damage. This reference teaches employing a 5 MHz transducer with a contact straight beam and calibrating to ensure a total of four back reflections. The reference further states that accurate thickness calibration identifies thinning as well as identifying hydrogen damage. The procedure is based on an attenuation principle.

Technical reference 3 shows a series of oscilloscope traces taken with an ultrasonic frequency of about 9.8 MHz used on water filled tubes. In this particular case, the deposit was of intermediate density and the influence on the ultrasonic pattern was about an average between scale conditions that produced both stronger and weaker effects. The reference states that if physical properties of the scale, such as density, particular size, etc. remain reasonably constant then the decay rate of the echo train should correlate quite well with the thickness of the deposit. The tubes must be water-filled for this method to operate, however.

SUMMARY OF THE INVENTION

The method of the present invention uses a contact transducer that is capable of transmitting and receiving ultrasonic energy at a nominal frequency of about 5 MHz. Ultrasonic energy from the transducer enters a dry boiler waterwall tube and travels until it reaches the inner surface of the empty tube where it is mostly reflected back toward the transducer. When a low density deposit is present, some of this energy is not reflected back but rather is absorbed by the deposit. The amount of energy that is lost to absorption in the deposit varies depending upon the amount of deposit present on the inner surface. Four reflected signals are displayed on a digital flaw detector (oscilloscope) and the signals are numbered. The signals are digitized and gated so that only the first and fourth backwall reflections are used. A computer calculates the waveform energy of each of the two pulses and also measures their amplitudes. From these measurements, values for signal attenuation are calculated and comparatively quantified based on the amount of inner surface deposit present on standard tubes.

The fourth reflection is used as a compromise between having several reflections which can be totalled or averaged, and having a selected pulse which is still high enough to avoid loss of resolution with resulting errors in the analog-to-digital conversion. For other tubes, however, either the third or the fifth back reflections might be optimum.

The present invention is distinct from earlier references which teach the use of passing ultrasonic energy through the deposit layer and through water filling the tube. The prior technique introduces transmission losses and additional losses due to scattering.

Any effects of deposit related scattering of the reflected signal in the present invention, is not a factor because the reflecting surface is not the deposit but rather the smoother metal/deposit interface. Transmission losses are also not a factor due to a high impedance mismatch at the inner surface of the dry tube. This condition will not allow the sound to travel through the deposit but just reflect back at the metal/deposit interface. It should be noted that the procedure as described in Technical reference 3 for example will not work on an empty (dry) tube.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

The only FIGURE in the drawing is a schematic representation of apparatus used for practicing the present invention.

DESCRIPTION OF THE PREFERRED EMBODIMENT

The formation inner surface deposits in waterwall tubing of boilers has become a major problem for fossil power plants. Because of its low density and inability for sufficiently propagating sound, these deposits could not be detected by using available techniques.

As demonstrated in the discussion of the prior art, many techniques are currently used for inspecting boiler components which utilize ultrasonic signals. Ultrasound is defined as any sound wave that has a frequency of 20,000 Hz or higher. In order to produce and introduce the sound waves into a material, transducers such as transducers 14 are utilized. These transducers generally include a piezoelectric crystal that vibrates at the desired frequency when excited by a pulsating voltage field. The ultrasonic sound produced can also be reflected by various surfaces and received back into the same transducer where, in reverse fashion, ultrasonic vibrations produce electrical signals which can be read by electrical equipment.

Referring to the drawing in particular, the invention embodied therein comprises a method of determining the presence of low density deposits 10 on the inner surface of a steel boiler waterwall tube 12 using an ultrasonic transducer 14 engaged against the outer surface 16 of the tube 12. Ultrasonic signals generated by the transducer 14 are directed toward the inner surface 18 of the tube and are reflected therefrom back and forth between the inner and outer surfaces of the tube.

According to the present invention, the contact transducer 14 is operated at a nominal frequency of 5 MHz.

A 5 MHz transducer was chosen for the invention primarily due to the performance of that frequency when compared to others in the lab. However, superior performance using a 5 MHz transducer does appear to be plausible.

There are three major factors that will effect the results of the invention with a change in transducer frequency. These are beam spread, material attenuation and sensitivity to low density deposits. The invention measures the total attenuation between the first and fourth sound reflections inside the tube wall. The total attenuation that is measured can dramatically be effected by a change in frequency through the three mechanisms mentioned above, more specifically, the amount the ultrasonic beam spreads out as it travels through the material, the amount the material (tube wall) scatters and/or attenuates the signal and the amount of signal that is absorbed into the deposit. Therefore in order to optimize the invention, the frequency should be chosen to reduce the effects that beam spread and material attenuation have on the total attenuation and increase the attenuation due to the absorption of the deposit.

In order to decrease beam spread, the frequency of the transducer should be kept as high as possible. An increase in frequency will cause the ultrasonic beam to become more directional with less tendency for it to spread. This higher frequency will assure a higher energy density from the fourth reflection making its response (ignoring other effects) stronger. Too low a frequency will cause such beam spread that a significant portion of the beam will not even be received by the transducers.

Another factor that improves with higher frequencies is the absorption of sound by the deposit. Because of the deposit's low density (mass) and porous like structure, it is more likely to absorb or damp out the higher frequencies.

While from this, it would seem that the optimum transducer would operate at the highest frequency commercially available, material attenuation experienced in the tube wall will not allow this. Material attenuation increases exponentially as frequency increases. In fact, for steel, the material attenuation starts to increase dramatically between 5 to 10 MHz. If too high a frequency is used, the invention will not operate due to the inability of the sound to penetrate through the tube wall and back four times. It is important that the signals of interest maintain sufficient amplitude in order the maximize the accuracy of the calculations performed on the digitized signals.

In summary, rough guidelines or estimates for the frequency are:

<3 MHz—loose sensitivity to deposit and beam spread problem 3-7 MHz—optimum frequency range 7-15 MHz—loose accuracy of data due to material attenuation >15 MHz—cannot perform test due to lack of sufficient penetration.

Due to the sound transmitting characteristics of low density deposits 10, and the use of tube 12 when it is dry or empty, most of the ultrasonic energy from transducer 14 is reflected back toward the outer surface 16 of the tube. Four back and forth reflections are used in accordance with the present invention.

While ultrasonic energy does not readily pass through the low density deposit, some energy is absorbed by the deposit at 26, 27, 28 and 29, and thus removed from the reflected energy. The amount of energy that is absorbed by the deposit depends upon the amount of deposit present on the inner surface 18. Small amounts of deposit absorb less energy than larger amounts. The relationship between the energy absorption and deposit weight in grams per square foot, is advantageously used according to the present invention to quantitatively determine the amount of low density deposit.

According to the present invention, the first four reflections numbered 1, 2, 3 and 4 in the figure, are displayed on a digital flaw detector such as oscilloscope 20. The signals are numbered on the display so that the paths traveled can be clarified. The signals are digitized and gated so that only the first and fourth reflections are used. Signals number 2 and 3 are discarded. The two digital signals (the first and the fourth) are then sent to a computer 22 for analysis. The computer calculates waveform energy of each of the two pulses and also measures their amplitudes. From these measurements, values for signal attenuation are calculated as follows:

Relative Signal Amplitude = 20 log (A1/A2) or
Relative Signal Energy = 10 log (E1/E2)
(Decibels/three reflections) where,
A1 = Amplitude of pulse 4
A2 = Amplitude of pulse 1
E1 = Waveform energy of pulse 4
E2 = Waveform energy of pulse 1

(When calculating decibels using the above equations, a negative result indicates signal attenuation).

Variations in this attenuation measurement are mostly due to reflected energy away from the direction of the transducer, material transmission losses and absorption of sound energy by inner surface deposits. If the angle of sound propagation, geometries, material thicknesses and surface conditions are held to a constant, then any changes in the attenuation measurements are a direct result of sound absorption by inner surface deposits. Since sound absorption increases with increasing deposit buildup, a direct comparative test of the severity of this buildup can be made through attenuation measurements. Displayed results are viewed at 24. Absorption of ultrasonic energy in deposit 10 is shown at 26, 27, 28 and 29 for each reflection.

Low density deposits can significantly lower the efficiency level at which a boiler can perform. This deposit is removed by carefully cleaning the tubes with various chemical flushes. The effectiveness of this chemical cleaning, is highly dependent upon the analysis of a "worst case" sample tube. Currently tube samples are randomly removed from the boiler for chemical analysis with no assurance that a "worst case" sample was taken. With the present invention, tube samples can be selected based on deposit buildup. The heavier the buildup the better the analysis.

The system of the invention can also be made portable for easier use.

While a specific embodiment of the invention has been shown and described in detail to illustrate the application of the principles of the invention, it will be understood that the invention may be embodied otherwise without departing from such principles.

What is claimed is:

1. A method of quantifying low density deposits on an inner surface of a boiler waterwall tube having an outer surface, comprising the steps of:

positioning an ultrasonic transducer on the outer surface of the tube across from an area to be inspected on the inner surface of the tube;

directing ultrasonic energy from the outer surface toward the inner surface of the tube, the ultrasonic energy reflecting at a metal/deposit interface on the inner surface a plurality of times between the metal/deposit interface on the inner surface and the outer surface, the ultrasonic transducer receiving each of the reflections, each reflection from the metal/deposit interface on the inner surface being attenuated by a high porosity level of the low density deposit on the inner surface;

collecting analog signals with the ultrasonic transducer corresponding to the first and fourth reflection of ultrasonic energy from the metal/deposit interface on the inner surface;

digitizing the analog signals from the first and fourth reflections; and analyzing the first and fourth digital signals for attenuation for quantifying the low density deposit on the inner surface of the tube.

2. A method according to claim 1, including determining the buildup of low density deposits when the tube is empty of water.

3. A method according to claim 1 including calculating from the digitized signals, the waveform energy of the first reflection and the waveform energy of the fourth reflection, and analyzing attenuation by taking the logarithm of the fraction of the waveform energy of the fourth reflection divided by the waveform energy of the first reflection, and multiplying the logarithm by a constant for the conversion to decibels.

4. A method according to claim 3, wherein the constant is 10, which is necessary for the conversion of bels to decibels.

5. A method according to claim 1 including analyzing the attenuation by taking the logarithm of the fraction comprising the amplitude of the fourth reflection divided by the amplitude of the first reflection, and multiplying the logarithm by a constant.

6. A method according to claim 5, wherein the constant is 20, which is necessary for the proper conversion of bels to decibels.

* * * * *